(12) United States Patent
Martin et al.

(10) Patent No.: US 12,167,840 B2
(45) Date of Patent: Dec. 17, 2024

(54) ATTACHMENT ASSEMBLY AS WELL AS VIDEO LARYNGOSCOPE SYSTEM

(71) Applicant: HEINE Optotechnik GmbH & Co. KG, Gilching (DE)

(72) Inventors: Timo Martin, Dettenschwang (DE); Felix Michel, Munich (DE); Konrad Entsfellner, Gilching (DE)

(73) Assignee: HEINE Optotechnik GmbH & Co. KG, Gilching (DE)

( * ) Notice: Subject to any disclaimer, the term of this patent is extended or adjusted under 35 U.S.C. 154(b) by 198 days.

(21) Appl. No.: 17/847,033

(22) Filed: Jun. 22, 2022

(65) Prior Publication Data

US 2022/0409038 A1 Dec. 29, 2022

(30) Foreign Application Priority Data

Jun. 23, 2021 (DE) ...................... 10 2021 116 266.1

(51) Int. Cl.
*A61B 1/267* (2006.01)
*A61B 1/00* (2006.01)
*A61B 17/00* (2006.01)

(52) U.S. Cl.
CPC .......... *A61B 1/267* (2013.01); *A61B 1/00062* (2013.01); *A61B 1/00066* (2013.01); *A61B 1/00096* (2013.01); *A61B 1/00101* (2013.01); *A61B 1/00137* (2013.01); *A61B 2017/0023* (2013.01)

(58) Field of Classification Search
CPC ................. A61B 1/267; A61B 1/00062; A61B 1/00066; A61B 1/0052; A61B 1/053; A61B 1/00142; A61B 1/051; A61B 1/00096; A61B 1/00101; A61B 1/00137; A61B 2017/0023
USPC ....................................................... 348/744
See application file for complete search history.

(56) References Cited

U.S. PATENT DOCUMENTS

| | | | |
|---|---|---|---|
| 8,029,440 B2 * | 10/2011 | Birnkrant ............... | A61B 1/051 600/188 |
| 9,782,061 B2 * | 10/2017 | Newcomb ............ | A61B 1/0684 |
| 10,299,668 B2 * | 5/2019 | Walker ............... | A61B 1/00042 |
| 10,835,115 B2 * | 11/2020 | Inglis ................. | A61B 1/00124 |

(Continued)

FOREIGN PATENT DOCUMENTS

| | | |
|---|---|---|
| WO | 2016074894 A2 | 5/2016 |
| WO | 2022081509 A1 | 4/2022 |

*Primary Examiner* — Brian P Yenke
*Assistant Examiner* — Sean N. Haiem
(74) *Attorney, Agent, or Firm* — Dilworth IP, LLC

(57) ABSTRACT

An attachment assembly for a camera arm of a video laryngoscope including a spatula and a protective cap, wherein the spatula has a base body with a handle end and a patient end opposite the handle end as well as a channel formed in the base body for receiving the camera arm, wherein the channel is open both towards the handle end and towards the patient end, wherein the protective cap is a component part separate from the spatula, is insertable into the channel and includes an at least partially transparent protective section, wherein the protective cap is designed such that a tip of the camera arm of the video laryngoscope can be engaged in the protective section and to be covered by the protective section. Moreover, a video laryngoscope system is shown.

18 Claims, 2 Drawing Sheets

(56) References Cited

U.S. PATENT DOCUMENTS

| | | | |
|---|---|---|---|
| 2002/0022769 A1* | 2/2002 | Smith | A61B 1/267 |
| | | | 600/188 |
| 2014/0160261 A1* | 6/2014 | Miller | A61B 1/05 |
| | | | 348/77 |
| 2016/0206188 A1* | 7/2016 | Hruska | A61B 1/0684 |
| 2018/0168433 A1* | 6/2018 | Meyer | A61B 1/00016 |
| 2019/0133430 A1* | 5/2019 | Inglis | A61B 1/00052 |
| 2022/0000354 A1* | 1/2022 | Stoffel | A61B 1/00101 |

\* cited by examiner

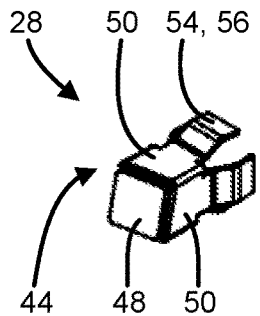
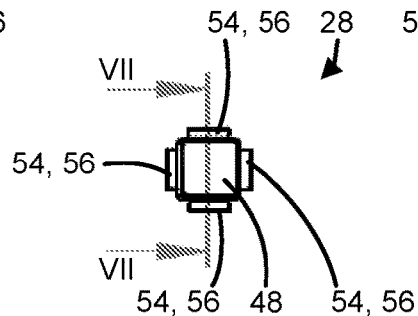
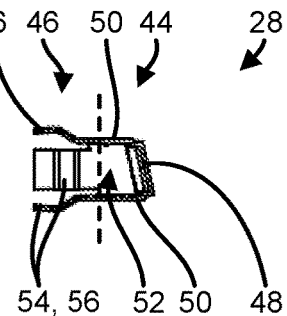
Fig. 5    Fig. 6    Fig. 7
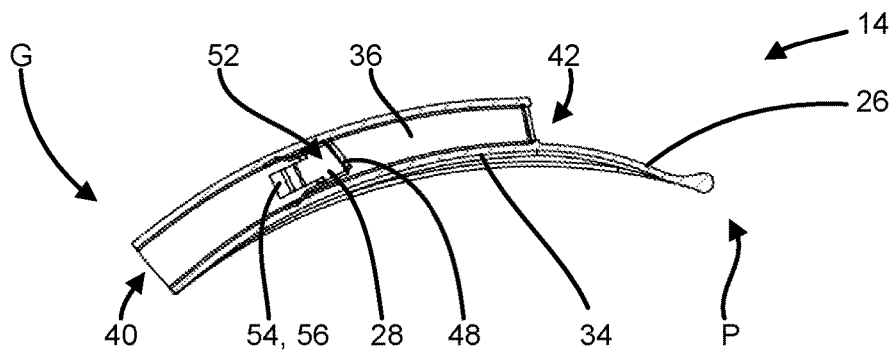
Fig. 8
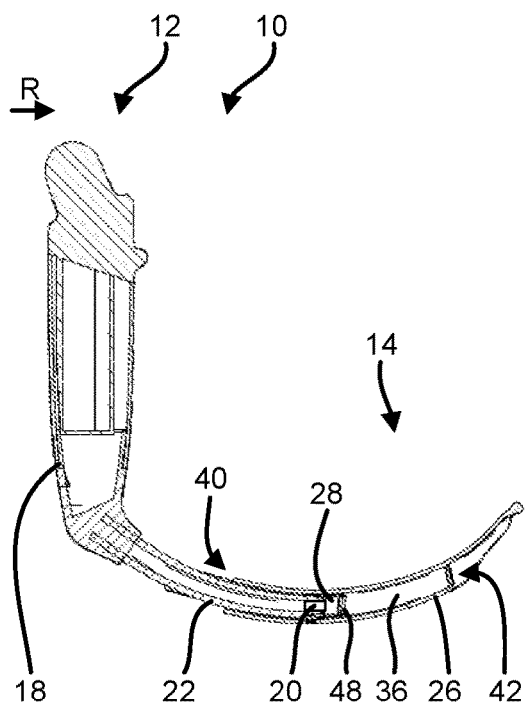
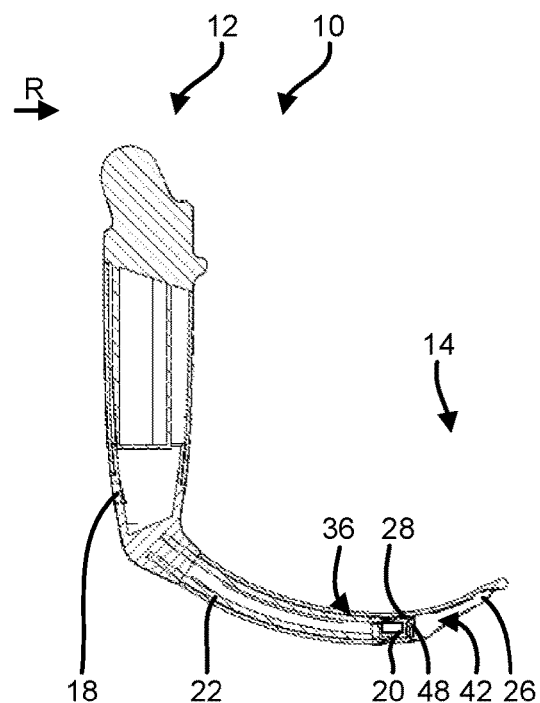
Fig. 9    Fig. 10

ATTACHMENT ASSEMBLY AS WELL AS VIDEO LARYNGOSCOPE SYSTEM

FIELD OF THE DISCLOSURE

The disclosure relates to an attachment assembly for a camera arm of a video laryngoscope as well as a video laryngoscope system with a video laryngoscope comprising a camera arm.

BACKGROUND

Video laryngoscopes with camera arms are known. In such video laryngoscopes, spatulas for laryngoscopies are mounted on the camera arm to protect the camera of the camera arm and also the camera arm itself from contamination during the laryngoscopy. As a result, the cost of cleaning the camera arm and thus the entire video laryngoscope is reduced. The spatulas are exchanged after every patient examination and are sterilised in the case of reusable spatulas or disposed of in the case of disposable spatulas.

To this end, disposable spatulas are known which are formed as a single piece and comprise a channel in which the camera arm is inserted. The channel is closed on the patient side so that the camera and the camera arm are encapsulated completely by the spatula. The camera field of view must thus run on the patient-side end of the channel through the spatula, thereby resulting in the material properties of the spatula being subject to strict material conditions. In particular, a spatula must be made of a transparent material. This results in less flexibility in the manufacture of disposable spatulas, wherein in particular disposable spatulas cannot be manufactured from recycled material as recycled material does not have the required optical properties.

SUMMARY

Thus, there is provided a video laryngoscope system as well as an attachment assembly for a video laryngoscope, in which the material of the spatula must fulfil fewer requirements, in particular optical requirements.

It is provided an attachment assembly for a camera arm of a video laryngoscope comprising a spatula and a protective cap. The spatula has a base body comprising a handle end and a patient end opposite the handle end as well as a channel formed in the base body for receiving the camera arm, wherein the channel is open both towards the handle end and towards the patient end. The protective cap is a component part separate from the spatula, is insertable into the channel and comprises an at least partially transparent protective section, wherein the protective cap is designed such that a tip of the camera arm of the video laryngoscope can be engaged in the protective section and is covered by the protective section.

As a separate component part, the protective cap can be moved, in particular, relative to the base body.

In particular, the camera field of view runs at the tip of the camera through the protective section and not through the base body if the tip of the camera arm is fixed in place in the protective section.

As a result of the protective cap that is separate from the spatula, the spatula must no longer cover the camera arm and, in particular the camera at the tip of the camera arm so that the spatula itself may fulfil fewer material requirements, in particular the spatula does not have to be transparent.

Furthermore, it has been recognised that the channel must not be completely sealed at the patient-side end in order to protect the camera arm sufficiently from contamination.

The base body can have a Macintosh, Miller, Dörges or McCoy design. For example, the spatula comprises the base body completely.

The protective section can also be completely transparent.

In particular, the protective cap is not a part of the camera arm, but instead a part of the attachment assembly separate from the camera arm. For example, the protective cap makes contact with the camera arm only during insertion of the camera arm into the channel or shortly before the camera arm is inserted into the channel.

In an embodiment, the protective cap in the use state of the attachment assembly is located in the area of the patient-side end of channel, in particular the protective cap extends at least partially through the patient-side opening of the channel. This ensures that the protective cap protects the camera arm and the camera field of view proceeds as intended.

For example, the protective cap in the starting state of the attachment assembly is located within the channel and comprises an attachment section that positions the protective cap in a starting position in relation to the base body, in particular wedges the protective cap into the channel.

The positioning is undertaken, for example, by the manufacturer and is detachable, e.g., by means of the camera arm.

The user's use is simplified by the positioning of the protective cap in the starting state by the manufacturer. At the same time, it ensures that the protective cap is fitted on the camera arm correctly as the user will insert the camera arm further into the channel than the starting position.

The starting position can be between the handle-side opening and the patient-side opening of the channel and/or differ from the position of the protective cap in the use state.

In an embodiment of the disclosure, the attachment section comprises at least two, in particular four wings, extending from the opposing sides of the protective section, wherein said at least two wings rest on the corresponding channel walls of the channel and/or wherein the wings extend further outwards than the protective section. By means of the wings, the protective cap is positioned in the channel easily.

The wings are particularly elastic so that they can be prestressed against the channel walls in the starting position.

Outwards in relation to a centre line of the receiving means or the channel can be understood as radially outwards.

To determine the position of the protective cap and thus camera field of view exactly, at least a stop can be provided in the channel on its patient-side end, on said stop the protective cap, in particular the protective section rests in the use state.

In an embodiment, the protective section comprises a transparent front pane and at least two, in particular four sides, wherein the sides extend from the front pane and form a receiving means for the tip of the camera arm, in particular wherein the sides run parallelly and/or the front pane is arranged obliquely to the sides. By means of the receiving means, the tip of the camera arm is positioned reliably.

The front pane can completely seal the receiving means on the patient side.

For example, the wings extend from the sides, in particular on the edge of the sides facing away from the front pane.

To manufacture the spatula simply and/or in an environmentally friendly manner, the spatula can be made of a non-transparent material and/or made of an at least mainly, in particular completely recycled material.

In an embodiment, the patient-side opening of the channel is located between the handle end and the patient end of the base body, in particular in the middle third between the handle end and the patient end, allowing the spatula to be designed thinly on the patient end to reduce the risk of injury.

The base body has, for example, a projecting part between the patient end and the end of the channel.

The channel can be closed along its outer edge, in particular along the entire length of the channel in order to protect the camera arm reliably.

The cross section of the channel can reduce in size from the handle-end opening of the channel to the patient-side opening of the channel, in particular the height of the cross section can reduce in size, thereby simplifying the insertion of the camera arm into the channel.

In an embodiment, the base body has a width traverse to the insertion direction, wherein the channel extends only across a part of the width, in particular exactly half or less than half of the width. In this way, a classic visual examination is facilitated, i.e., without camera support.

The base body and/or the protective cap can be designed as a single piece in order to manufacture cost-effectively.

For example, the base body and/or the protective cap are each an injection-moulded part.

Moreover, the object is solved by a video laryngoscope system with a video laryngoscope comprising a camera arm as well as an attachment assembly for the camera arm as previously described.

The features and advantages described for the attachment assembly equally apply to the video laryngoscope system and vice versa.

For example, the camera arm comprises a tip with a camera, wherein in the use state the tip is fixed in place in the protective cap, in particular in the receiving means of the protective cap, and the camera arm extends through the channel. In this way, both the camera and the camera arm are protected sufficiently from contamination.

In particular, the camera field of view runs through the front pane towards the patient-side end of the base body.

The camera arm holds, for example, both the spatula as well as the protective cap within the spatula.

In an embodiment, the video laryngoscope system is designed in such a way that the camera arm pushes the protective cap along from the starting position when inserting the camera arm into the channel of the spatula and pushes it to the patient-side opening of the channel until the state of use is attained, thereby making the use of the spatula extremely simple.

In an embodiment, the video laryngoscope system comprises a dispenser for the protective cap which is separate from the camera arm and the spatula, said the dispenser comprising a housing with a dispenser opening, and wherein the protective cap is provided within the housing in the area of the dispenser opening. In this way, the protective caps can be provided separately from the spatula.

BRIEF DESCRIPTION OF THE DRAWINGS

Additional advantages and features of the disclosure can be found in the following description as well as in the attached drawings to which reference is made. In the drawings:

FIGS. 5, 6, 7 show a protective cap of the attachment assembly according to the disclosure according to FIG. 1 in a perspective view, a front view and a sectional view.

FIG. 8 shows the attachment assembly according to the disclosure according to FIG. 1 in section in the starting state, and FIGS. 9,10 show the attachment assembly according to FIG. 8 in which the camera arm of the video laryngoscope is inserted in the starting state or in the use state.

DETAILED DESCRIPTION

Lists having a plurality of alternatives connected by "and/or", for example "A, B and/or C" are to be understood to disclose an arbitrary combination of the alternatives, i.e., the lists are to be read as "A and/or B and/or C". The same holds true for listings with more than two items.

Figure 1:
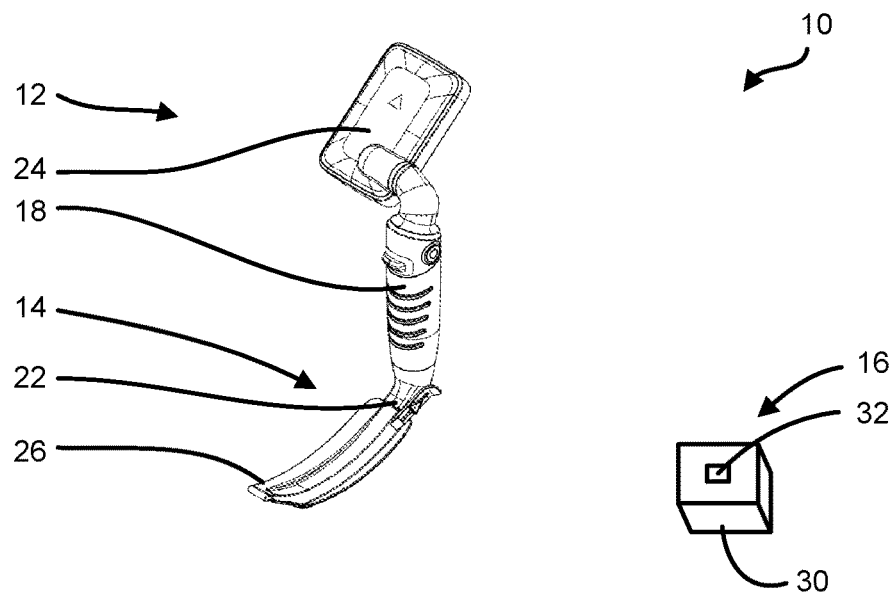
FIG. 1 shows a video laryngoscope system according to the disclosure comprising an attachment assembly according to the disclosure in a perspective view.

FIG. 1 shows a video laryngoscope system 10 comprising a video laryngoscope 12, an attachment assembly 14 as well as an optional dispenser 16.

The video laryngoscope 12 has a handle 18 and a camera arm 20 extending from it, on the tip of said camera arm 20 facing away from the handle 18 a camera 22 is arranged.

Moreover, a screen 24 that reproduces the image taken by the camera 22 can be provided on the handle 18.

The attachment assembly 14 comprises a spatula 26 as well as protective cap 28 (FIG. 5) for the camera 22, wherein the protective cap 28 is attached to the camera arm 20.

The optional dispenser 16 is a dispenser for protective caps 28 and has a housing 30 in which a dispenser opening 32 is designed.

Figure 2:
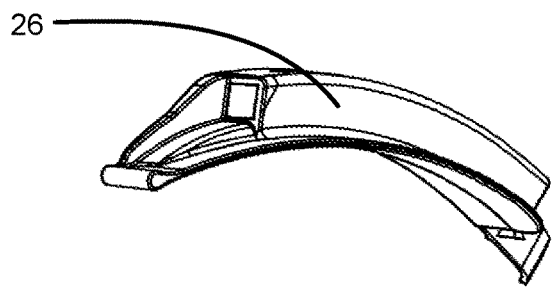
FIGS. 2, 3, 4 show a spatula of the attachment assembly according to the disclosure according to FIG. 1 in a perspective view, a front view and a sectional view.
Figures 3, 4:
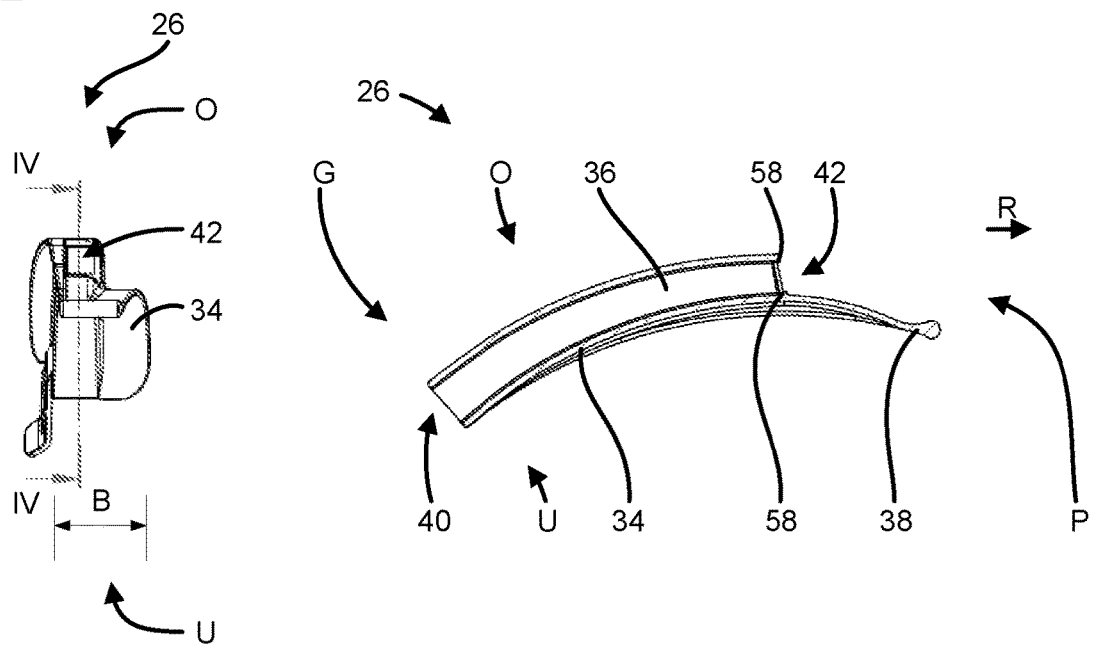

In FIGS. 2, 3 and 4, the spatula 26 of the attachment assembly 14 is shown in a perspective view, in a front view on the patient-side end P of the spatula 26 and in a sectional view.

The spatula 26 has a base body 34, in particular comprising the base body 34. For example, the spatula 26 is a disposable product, thus a disposable spatula.

The base body 34 is formed as a single piece, for example as an injection-moulded part. The material of the base body 34 is non-transparent and, for example, mainly, in particular completely a recycled material.

The base body 34 has a handle end G that faces the handle 18 of the video laryngoscope 12 as well as a patient end P that is opposite the handle end G, i.e. facing away from the handle 18, and faces the patient or is introduced into the patient.

In addition, the base body 34 has a bottom side U that rests on the patient, in particular the patient's tongue, during the examination. The opposite side of the base body 34 is the top side O.

In the shown embodiment, the base body 34 has a Macintosh design, i.e. the bottom side U of the base body 34 is curved. The base body 34 can of course be another design, such as a Miller, Dörges or McCoy design.

The insertion direction R extends from the handle end G towards the patient end P. The spatula 26 has a width B horizontally traverse to the insertion direction R (FIG. 3).

A channel 36 is designed for the camera arm 20 in the base body 34. The channel 36 extends from the handle end G on the top side O of the spatula 26 towards the patient end P.

For example, the channel 36 ends in the middle third between the handle end G and the patient end P. The remaining part of the base body 34 between the end of the channel 36 and the patient end P is this a projecting part 38 or a tongue.

In the traverse direction, it extends across half the width B or less of the base body 34, in particular asymmetrically and/or starting from a side.

The channel 36 is restricted along its outer edge by the channel walls that are part of the base body 34. For example, the channel 36 is completely closed along its outer edge. In the shown embodiment, the channel 36 is completely closed along its entire length in the insertion direction R along its outer edge.

The channel 36 comprises a first opening on its end facing the patient end P that is termed the handle-side opening 40 as well as a second opening towards the patient end P that is termed the patient-side opening 42. The handle-side opening 40 and the patient-side opening 42 are in particular the only openings of the channel 36.

In the shown embodiment, the patient-side opening 42 is smaller than the handle-side opening 40. The cross section of the channel 36 thus reduces in size from the handle-side opening 40 towards the patient-side opening 42, in particular continuously.

To change the cross section, the expansion of the channel 36 can remain the same in the traverse direction and only the height of the cross section of the channel 36 can reduce in size, i.e., expanding perpendicular to the traverse direction and perpendicular to the insertion direction R.

The channel 36 is not sealed in particular through the patient-side opening 42 as is common in the prior art, for example, by means of a disc.

The cross section of the channel 36 is chosen in such a way that the camera arm 20 can be inserted into the channel 36 up to the patient-side opening 42.

In FIGS. 5, 6, and 7, the protective cap 28 is shown in a perspective view, in a front view, i.e., on the patient-side end, and in a sectional view.

The protective cap 28 is a component part separate from the spatula 26 and can also be formed as a single piece or as an injection-moulded part. The material of the protective cap 28 is transparent, in particular a transparent plastic.

The protective cap 28 has a protective section 44 and an attachment section 46, wherein the attachment section 46 adjoins the protective section 44 on the handle side in the shown embodiment.

The protective section 44 comprises a transparent front pane 48 that has in particular a form complementary to the patient-side opening 42 of the channel 36.

Four sides 50 that are in particular parallel to each other project towards the handle end from the front pane 48.

The sides 50 and the front pane 48 do not include any right angles in the shown embodiment so that the front pane 48 is arranged obliquely to the sides 50. It is also conceivable that the front pane 48 is perpendicular to the sides 50.

The sides 50 form together with the front pane 48 a receiving means 52 for the tip of the camera arm 20. The receiving means 52 is sealed completely on the patient side, in particular by the front pane 48.

The attachment section 46 adjoins the sides 50 on the handle side.

The attachment section 46 comprises at least an attachment means 54, by means of which the protective cap 28 can be positioned in the channel 36.

In the shown embodiment, the attachment means 54 are four wings 56, wherein each wing 56 extends in each case from one of the sides 50 to the handle end G and simultaneously outwards.

Alternatively or additionally, breakaway webs, a thin plastic skin, adhesive, in particular adhesive drops, and/or a film can be used as the attachment means 54.

The wings 56 extend in particular further outward in relation to a centre line of the receiving means 52 and further outward than the protective section 44.

The wings 56 are designed elastically so that they can be moved inward.

In FIG. 8, the attachment assembly 14 is shown in a starting state. In this starting state, the protective cap 28 is inserted into the channel 36. The protective cap 28 is in a starting position that is between the handle-side opening 40 and the patient-side opening 42. In particular, no part of the protective cap 28 extends in the starting position through the patient-side opening 42.

The protective cap 28 is positioned in the starting position by the attachment means 54, in the shown embodiment thus the wings 56.

In the shown embodiment, this occurs as the wings 56 rest on the channel walls of the channel 36 and are prestressed against the channel walls due to their elasticity. Thus, the protective cap 28 is wedged in its starting position and secured against falling out.

Alternatively or additionally, breakaway webs, a thin plastic skin, adhesive, in particular adhesive drops, and/or a film can hold the protective cap 28 in the starting position.

The positioning in the starting position is in any case detachable, i.e. that the protective cap 28 can be moved by normal, conscious use.

For example, the protective cap 28 and the spatula 26 are manufactured separately and the protective cap 28 is then positioned by the manufacturer in the channel 36 of the spatula 26 in the starting position. The starting state thus corresponds to state at sale.

To use the video laryngoscope system 10, the user assembles the attachment assembly 14 in the starting state to the video laryngoscope 12. More specifically, the user inserts the camera arm 20 into the channel 36 of the spatula 26.

The tip of the camera arm 20 then meets, as shown in FIG. 9, the protective cap 28 in its starting position. In doing so, the tip of the camera arm 20 is fixed in place in the receiving means 52, wherein the camera arm 20 is guided through the wings 56 into the receiving means 52.

The user then inserts the camera arm 20 even further into the channel 36, thereby removing the positioning of the protective cap 28 and moving the protective cap 28 from its starting position relative to the base body 34 towards the patient-side opening 42 of the channel 36.

In other words, the camera arm 20 pushes the protective cap 28 from its starting position along towards the patient-side opening 42.

In FIG. 10, the state of use is shown in which the camera arm 20 has been inserted into the channel 36 completely, i.e., the length necessary for proper use.

In this state of use, the protective cap 28 is located in the area of the patient-side end of channel 36 and extends at least partially through the patient-side opening 42 in the shown embodiment.

The camera arm 20 holds both the spatula 26 and the protective cap 28.

It is clearly evident that the front pane 48 protrudes through the patient-side opening 42. One or more stops 58 can be provided in the area of the patient-end of the channel 36 for the purpose of establishing the state of use, said stops 58 extending in the channel 36 and on which the protective cap 28 rests, for example the sides 50 of the protective cap 28 rest.

In the use state, the camera 22 is thus received in the receiving means 52 of the protective cap 28 and is protected against contamination by this. The remaining camera arm 20 is protected against contamination by the base body 34.

The field of view of the camera 22 runs through the front pane 48 in the direction of the patient end P in the use state.

This ensures the necessary protection of the camera 22 without impairing the quality of the recordings. At the same time, the material of the spatula 26 can be selected independently from the material of the protective cap 28, thereby reducing the requirements for the material properties of the spatula. As a result, non-transparent and recycled materials can be used for the spatula 26, thereby contributing protection of the environment.

After the examination, the camera arm 20 is removed from the spatula 26, more specifically from the channel 36. In doing so, the protective cap 28 can remain in the channel 36 or be pulled out together with the camera arm 20. In the first case, the use of the spatula 26 is easier; in the latter case, it is possible to dispose of the spatula 26 and the protective cap 28 separately from each other, thus enabling better recycling.

Instead of the positioning of the protective cap 28 in a starting state in the channel 36, it is also conceivable in an alternative embodiment that the channel 36 is initially empty and the protective caps 28 are provided in the optional dispenser 16.

Before use, a protective cap 28 is applied to the tip of the camera arm 20 by means of the dispenser 16 and the camera arm 20 together with the protective cap 28 is inserted into the channel 36 until the state of use is attained.

For this, a plurality of protective caps 28 are located in the housing 30 of the dispenser 16, said protective caps 28 being arranged in such a way behind the dispenser opening 32 that, for example, a protective cap 28 is attached to the tip of the camera arm 20 by inserting the camera arm 20 through the dispenser opening 32.

Alternative, at least one protective cap 28 can protrude through the dispenser opening 32 so that the camera arm 20 can be fixed in place in it.

The invention claimed is:

1. An attachment assembly for a camera arm of a video laryngoscope with a spatula and a protective cap,
    wherein the spatula has a base body comprising a handle end and a patient end opposite the handle end as well as a channel formed in the base body for receiving the camera arm, wherein the channel is open both towards the handle end and towards the patient end,
    wherein the protective cap is a component part separate from the spatula, is insertable into the channel and comprises an at least partially transparent protective section, wherein the protective cap is designed such that a tip of the camera arm of the video laryngoscope can be engaged in the at least partially transparent protective section and is covered by the at least partially transparent protective section,
    wherein the protective cap in a starting state of the attachment assembly is located within the channel and comprises an attachment section that positions the protective cap in relation to the base body in a starting position, and
    wherein the attachment section comprises at least two wings extending from opposing sides of the at least partially transparent protective section, wherein the at least two wings rest on corresponding channel walls of the channel and/or wherein the at least two wings extend further outwards than the at least partially transparent protective section.

2. The attachment assembly according to claim 1, wherein the protective cap in a use state of the attachment assembly is located in an area of a patient-side end of the channel.

3. The attachment assembly according to claim 1, wherein the protective cap in a use state of the attachment assembly extends at least partially through a patient-side opening of the channel.

4. The attachment assembly according to claim 1, wherein the protective cap wedges the protective cap into the channel.

5. The attachment assembly according to claim 1, wherein at least a stop is provided in the channel on its patient-side end, on said stop the protective cap rests in a use state.

6. The attachment assembly according to claim 1, wherein the at least partially transparent protective section comprises a transparent front pane and at least two sides, wherein the sides extend from the transparent front pane and form a receiving means for the tip of the camera arm.

7. The attachment assembly according to claim 6, wherein the sides run parallel to one another and/or the transparent front pane is arranged obliquely to the sides.

8. The attachment assembly according to claim 1, wherein the spatula is made of a non-transparent material and/or made of an at least mainly recycled material.

9. The attachment assembly according to claim 1, wherein a patient-side opening of the channel is located between the handle end and the patient end of the base body.

10. The attachment assembly according to claim 1, wherein the channel is closed along its outer edge, and/or that a cross section of the channel reduces in size from a handle-end opening to a patient-side opening of the channel.

11. The attachment assembly according to claim 1, wherein a height of a cross section of the channel reduces in size.

12. The attachment assembly according to claim 1, wherein the base body has a width traverse to an insertion direction, wherein the channel extends only across a part of the width.

13. The attachment assembly according to claim 1, wherein base body is formed as a single piece and/or that the protective cap is formed as a single piece.

14. A video laryngoscope system with a video laryngoscope comprising a camera arm, and an attachment assembly for the camera arm according to claim 1.

15. The video laryngoscope system according to claim 14, wherein the camera arm comprises a tip with a camera, wherein in a use state the tip is fixed in place in the protective cap, and the camera arm extends through the channel.

16. The video laryngoscope system according to claim 14, wherein in a use state the tip is fixed in place in a receiving means of the protective cap.

17. The video laryngoscope system according to claim 14, wherein the video laryngoscope system is designed in such a way that the camera arm pushes the protective cap along from a starting position when inserting the camera arm into the channel of the spatula and pushes it to a patient-side opening of the channel until a use state is attained.

18. A video laryngoscope system, comprising:

a video laryngoscope comprising a camera arm;

an attachment assembly for the camera arm, the attachment assembly including a spatula and a protective cap, wherein the spatula has a base body comprising a handle end and a patient end opposite the handle end as well as a channel formed in the base body for receiving the camera arm, wherein the channel is open both towards the handle end and towards the patient end, and wherein the protective cap is a component part separate from the spatula, is insertable into the channel and comprises an at least partially transparent protective section, wherein the protective cap is designed such that a tip of the camera arm of the video laryngoscope can be engaged in the at least partially transparent protective section and is covered by the at least partially transparent protective section; and a dispenser for the protective cap which is separate from the camera arm and the spatula, the dispenser comprising a housing with a dispenser opening, wherein the protective cap is provided within the housing in an area of the dispenser opening.

\* \* \* \* \*